United States Patent [19]

Brunner et al.

[11] Patent Number: 4,803,268

[45] Date of Patent: Feb. 7, 1989

[54] PROCESS FOR THE PREPARATION OF CYCLOHEXANEDIONECARBOXYLIC ACID DERIVATIVES

[75] Inventors: Hans-Georg Brunner, Lausen; Urs Müller, Münchenstein, both of Switzerland

[73] Assignee: Ciba-Geigy Corporation, Ardsley, N.Y.

[21] Appl. No.: 8,445

[22] Filed: Jan. 29, 1987

Related U.S. Application Data

[63] Continuation of Ser. No. 778,109, Sep. 20, 1985, abandoned.

[30] Foreign Application Priority Data

Oct. 2, 1984 [CH] Switzerland ......................... 4734/84

[51] Int. Cl.$^4$ ..................... C07D 279/10; C07C 67/22
[52] U.S. Cl. .................................. 544/58.4; 544/172; 546/237; 546/238; 548/539; 556/117; 558/414; 560/116; 560/118; 560/125; 560/126; 562/500; 562/507; 562/508
[58] Field of Search .................... 71/94, 88, 95, 105, 71/106, 111, 113, 115, 118, 98; 560/116, 118, 125, 126; 562/500, 507, 508; 556/117; 558/414; 548/539; 544/172, 58.4; 546/237, 238

[56] References Cited

U.S. PATENT DOCUMENTS

| 4,440,566 | 4/1984 | Luo | 71/98 |
| 4,560,403 | 12/1985 | Motojima et al. | 71/106 |
| 4,618,360 | 10/1986 | Brunner | 71/88 |
| 4,623,382 | 11/1986 | Brunner | 71/94 |

FOREIGN PATENT DOCUMENTS

| 2039466 | 2/1972 | Fed. Rep. of Germany . |
| 2232730 | 1/1974 | Fed. Rep. of Germany . |
| 58-164543 | 9/1983 | Japan . |
| 558319 | 1/1975 | Switzerland . |

Primary Examiner—Paul J. Killos
Assistant Examiner—Vera C. Clarke
Attorney, Agent, or Firm—Kevin T. Mansfield; Edward McC. Roberts

[57] ABSTRACT

The present invention relates to a novel, optimized process for the preparation of cyclohexanedionecarboxylic acid derivatives of formula I which can be carried out in a single vessel affording a very good yield, which process comprises heating a reactive carboxylic acid derivative of formula III

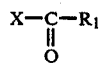 (III)

wherein X is a halide, an alkylsulfonic or arylsulfonic acid radical or the molecular radical

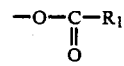

which is necessary to form an anhydride and $R_1$ is alkyl or cycloalkyl, with an alkali metal cyanide or copper cyanide, in an inert organic solvent, to give a mixture, then adding in succession to said mixture, at a temperature in the range from 0° C. to room temperature, zinc chloride, an equimolar amount, with respect to the carboxylic acid derivative of formula III, of a 3,5-cyclohexanedione-1-carboxylic acid derivative of formula II

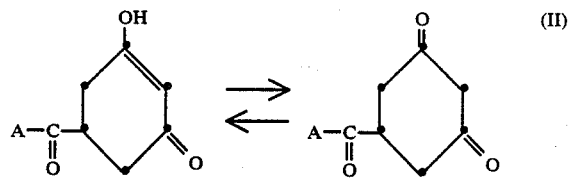 (II)

wherein A is an ester or amide radical, and, dropwise, an amine, and, after acidifying the reaction mixture with an aqueous acid, isolating the resultant 4-acyl-3,5-cyclohexanedione-1-carboxylic acid derivative of formula I

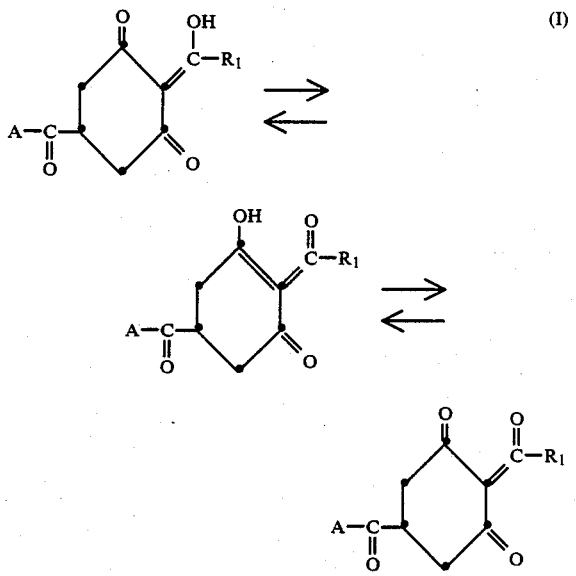 (I)

by extraction.

Said cyclohexanedionecarboxylic acid derivatives have herbicidal and plant growth regulating properties.

9 Claims, No Drawings

PROCESS FOR THE PREPARATION OF CYCLOHEXANEDIONECARBOXYLIC ACID DERIVATIVES

This is a continuation of application Ser. No. 778,109 filed on Sept. 20, 1985, abandoned.

The present invention relates to a novel, optimised process for the preparation of cyclohexanedionecarboxylic acid derivatives with herbicidal and plant growth regulating properties. The invention also relates to novel products, as well as to compositions which contain said cyclohexanedionecarboxylic acid derivatives and to the use thereof for controlling weeds or regulating plant growth.

The cyclohexanedionecarboxylic acid derivatives of the present invention are 4-acyl-3,5-cyclohexanedione-1-carboxylic acid derivatives of formula I

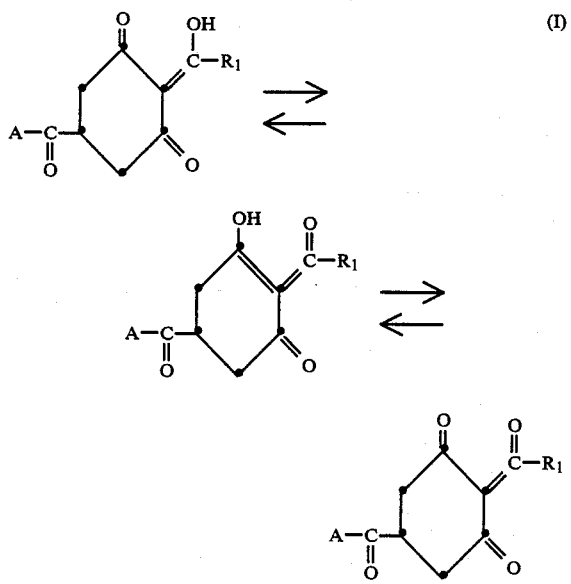

wherein

A is an $OR_2$ or $-NR_3R_4$ radical or a metal or ammonium salt thereof, $R_1$ is $C_1$–$C_6$alkyl or $C_3$–$C_6$cycloalkyl, each unsubstituted or substituted by halogen, $C_1$–$C_4$alkoxy or $C_1$–$C_4$alkylthio, $R_2$, $R_3$ and $R_4$ are each independently hydrogen, $C_1$–$C_6$alkyl, $C_1$–$C_4$haloalkyl, $C_2$–$C_{10}$alkoxyalkyl, $C_2$–$C_{10}$alkylthioalkyl; $C_3$–$C_6$alkenyl which is unsubstituted or substituted by halogen, $C_1$–$C_4$alkoxy or $C_1$–$C_4$alkylthio; $C_3$–$C_6$alkynyl; or phenyl wherein the phenyl nucleus is unsubstituted or substituted by halogen, $C_1$–$C_4$alkyl, $C_1$–$C_4$alkoxy, $C_1$–$C_4$haloalkyl, nitro or cyano, and $R_3$ and $R_4$, together with the nitrogen atom to which they are attached, also form a 5- or 6-membered heterocyclic ring system which may contain an additional oxygen or sulfur atom in the ring.

In the above definitions the alkyl radicals comprise both straight chain and branched radicals, e.g. methyl, ethyl, propyl, isopropyl, butyl, isobutyl, sec-butyl, tert-butyl, as well as all stereoisomers of the higher homologues. Alkenyl and alkynyl also comprise straight chain and branched radicals, e.g. vinyl, allyl, methallyl, butenyl, methylbutenyl and dimethylbutenyl, ethynyl, propynyl, butynyl, methylbutynyl and dimethylbutynyl.

Halogen is fluorine, chlorine, bromine or iodine.

A 5- or 6-membered heterocyclic ring system $-NR_3R_4$ which may contain an additional oxygen or sulfur atom in the ring is pyrrole, pyrrolidine, piperidine, morpholine or also thiomorpholine. These rings may also be substituted by methyl The salts of these compounds are obtained with bases. Suitable bases are preferably alkali metal hydroxides, alkaline earth metal hydroxides, iron, copper, nickel and zinc hydroxides, and also ammonia or quaternary $C_1$–$C_4$alkylammonium or $C_1$–$C_4$hydroxyalkylammonium bases.

The cyclohexanedionecarboxylic acid derivatives of formula I have good herbicidal and plant growth regulating properties. Under normal conditions they are solid or viscous compounds and no special precautionary measures are required for handling them.

In the literature processes have been described in accordance with which such compounds and similar ones are prepared or could be prepared. In all of these processes intermediates have to be isolated before being further reacted, which complicates operational procedures and reduces the yield.

In Japanese published application No. 58 164 543 for example such compounds are prepared in 60–72% yield by adding an acid chloride to a 3,5-cyclohexandione-1-carboxylate, adding an acid chloride to the resultant 3-acyloxycyclohex-3-ene-5-onecarboxylate and then converting the resultant 3-acyloxycyclohex-3-ene-5-onecarboxylate into the desired 4-acyl-3,5-cyclohexanedione-1-carboxylic acid derivative by boiling for several hours in toluene in the presence of a catalytic amount of dimethylaminopyridine (γ-picoline, 4-pyrrolidinoaminopyridine, N-methylimidiazole etc.).

European published application No. 90 262 discloses a process for the preparation of 2-benzoyl-1,3-cyclohexanediones, in accordance with which process 1,3-cyclohexanedione is combined with benzoyl cyanide in the presence of zinc chloride and an organic base. The condensation product is isolated, dissolved in ether and converted with copper acetate into a copper complex salt which is isolated by filtration from the reaction mixture. The copper complex salt is then dissolved in hydrochloric acid and the desired 2-acyl-1,3-cyclohexanedione can then be isolated from the acidic solution by extraction. Also in this prepratory process, the yield of which is indicated as being 78%, intermediates are isolated twice. The preparation of the starting benzoyl cyanide in accordance with Org. Synthesis Coll., Vol. III (1955), p 122, wherein the benzoyl chloride is combined with a metal cyanide under the specific precautionary measures, is not taken into account.

2-Acyl-1,3-cyclohexanediones can also be prepared in accordance with Synthesis 925 (1978) by condensing, in a first step, the 1,3-cyclohexanedione with an acid chloride, in the presence of an inert organic solvent and an organic base. The resultant acyloxycyclohex-3-ene-3-one is isolated and, in a second step, is rearranged in the presence of a Lewis acid such as aluminium trichloride to form the desired 2-acyl-3,5-cyclohexanedione.

Although said C-acylation catalysed by a Lewis acid was known, so far it has not been possible to apply or modify it successfully for the preparation of the 4-acyl-3,5-cyclohexanedione-1-carboxylates of the present invention.

In accordance with a novel optimised process, the cyclohexanedionecarboxylic acid derivatives of formula I can be prepared in excellent yield in a single reaction step. In said process a reaction vessel is charged with an acid halide, dissolved in an inert solvent, and a metal cyanide, preferably copper cyanide or an alkali metal cyanide. After brief heating, zinc chloride, a 3,5-cyclohexanedione-1-carboxylic acid derivative and finally, dropwise, an organic base are added in succession at a temperature in the range from 0° C. to room temperature. The reaction mixture is then acidified with an aqueous acid. The organic extract from which the solvent has been removed is the desired 4-acyl-1,3-cyclohexanedione-1-carboxylic acid derivative of formula I. In this process intermediates are not isolated, nor does the reaction vessel need to be changed.

The reaction sequence can be illustrated by the following scheme:

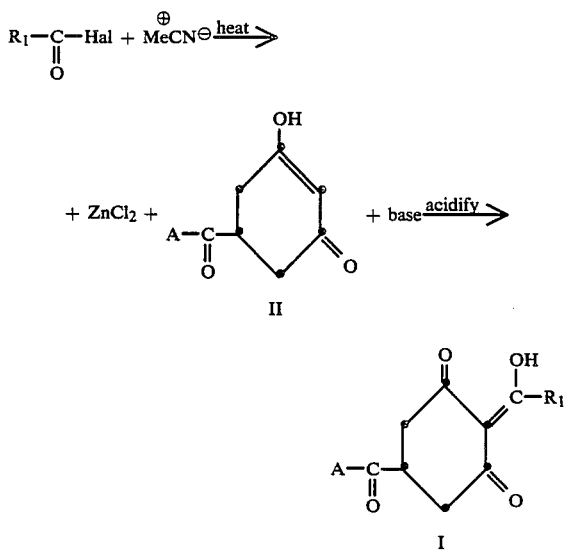

This reaction must first lead to the formation of the acid cyanide of formula

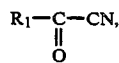

as intermediate, which reacts with the 3,5-cyclohexanedione-1-carboxylic acid derivative of formula II.

The novel process of the present invention makes it possible to prepare the 4-acyl-3,5-cyclohexanedione-1-carboxylic acid derivatives of formula I in virtually quantitative yield in a single reaction sequence without having to isolate the intermediates.

The process of the present invention for the preparation of cyclohexanedionecarboxylic acid derivatives of formula I comprises combining, in an inert solvent, a reactive carboxylic acid derivative of formula III

wherein X is a halogen atom, an alkylsulfonic or arylsulfonic acid radical or the molecular radical

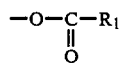

which is necessary to form an anhydride and $R_1$ is as defined for formula I, and a metal cyanide, heating the reaction mixture to boiling point and, after cooling to a temperature in the range from 0° C. to room temperature, adding in succession to said mixture a Lewis acid, an equimolar amount, with respect to the carboxylic acid derivative of formula III, of a 3,5-cyclohexanedione-1-carboxylic acid derivative of formula II

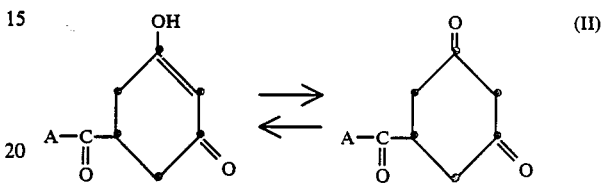

wherein A is as defined for formula I, and, dropwise, an organic base and, after acidifying the reaction mixture with an aqueous acid, isolating therefrom by extraction the 4-acyl-3,5-cyclohexanedione-1-carboxylic acid derivative of formula I.

Suitable inert organic solvents for this process are in particular acetonitrile, halogenated hydrocarbons such as chloroform, methylene chloride, ethylene chloride, (1,2-dichloroethane), as well as higher boiling ethers such as diisopropyl ether, dioxane or tetrahydrofuran, and higher boiling ketones such as methyl ethyl ketone, and also dimethylformamide and dimethyl sulfoxide.

It is preferred to employ as reactive acid derivative of formula III a halide such as the chloride or bromide.

The metal cyanides preferably employed in this reaction are copper cyanide, potassium cyanide or sodium cyanide or mixtures thereof.

It is advantageous first to heat the mixture of the reactive carboxylic acid derivative of formula III and the metal cyanide in an inert solvent for 1 to 25 hours under reflux before cooling and continuing the reaction at a temperature in the range from 0° C. to room temperature.

In this reaction it is preferred to employ zinc chloride as Lewis acid; however, aluminium chloride, antimony chloride and others may also be employed.

The following organic bases can be added dropwise to the reaction mixture: trimethylamine, diethylamine, triethylamine, γ-picoline, 4-N,N-dimethylpyridine, 4-N,N-diethylpyridine, 4-pyrrolidinopyridine, N-methylimidazole or 4-ethylimidazole. Further organic and inorganic bases are also possible for this purpose, but in practice the bases listed above have proved most suitable for ensuring a smooth and complete reaction course.

To complete the reaction, the mixture is acidified with an aqueous acid. The mixture of 6N hydrochloric acid and ice has proved most suitable. Two phases are formed; the organic phase consists essentially of the 4-acyl-3,5-cyclohexanedione-1-carboxylic acid derivative of formula I, whereas the salts and any non-reacted carboxylic acid or derivatives of formula III remain in the aqueous phase and are discarded.

Many compounds of formula I are known and e.g. described in Japanese published application No. 58 164 543. However, others are novel and have been prepared for the first time. The present invention also comprises these novel compounds. Those 4-acyl-3,5-cyclohexanedione-1-carboxylic acid derivatives of formula I, wherein A is an ester or amide radical as defined for formula I, are novel.

The following compounds have been prepared for the first time: 4-cyclopropylcarbonyl-3,5-cyclohexanedione-1-carboxylic acid, methyl and ethyl 4-cyclopropylcarbonyl-3,5-cyclohexanedione-1-carboxylate, ethyl 4-trimethylacetyl-3,5-cyclohexanedione-1-carboxylate, dimethyl 4-cyclobutylcarbonyl-3,5-cyclohexanedione-1-carboxamide, methylthiopropyl 4-butyryl-3,5-cyclohexanedione-1-carboxamide, diallyl 4-butyryl-3,5-cyclohexanedione-1-carboxamide, pyrrolidone 4-butyryl-3,5-cyclohexanedione-1-carboxamide, dimethyl 4-propionyl-3,5-cyclohexanedione-1-carboxamide and dimethyl 4-hexamoyl-3,5-cyclohexanedione-1-carboxamide.

The starting cyclohexanedionecarboxylic acid derivatives of formula II are, on the one hand, obtained by hydrogenating 3,5-dihydroxybenzoic acid with hydrogen and Raney nickel and subsequently esterifying or amidating the acid radical in accordance with the following reaction scheme:

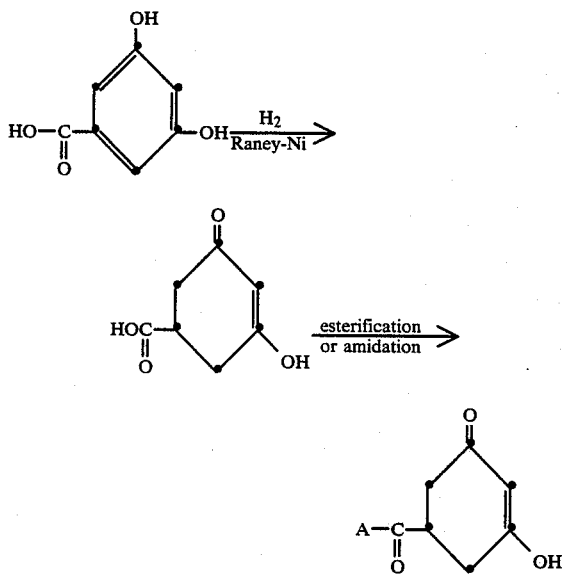

in which reaction the keto group may in some cases have to be protected, e.g. as enol ether or enamine, q.v. J. Am. Chem. Soc. 78, 4405 (1956).

However, it is also possible to hydrogenate a 3,5-dihydroxybenzoic acid derivative with hydrogen and Raney nickel in accordance with the reaction scheme:

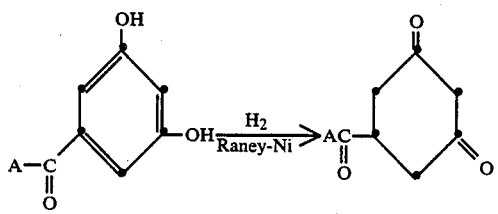

q.v. Arch. Pharm. 307, 577 (1974).

When used at low rates of application, the compounds of formula I have good selective growth inhibiting and selective herbicidal properties which make them most suitable for use in crops of useful plants, especially in sugar cane, cereals, cotton, soybeans, maize and rice.

The mode of action of these compounds is unusual. Many are translocatable, i.e. they are absorbed by the plant and transported to other parts of it where they then exert their action.

In addition the compounds of formula I have pronounced plant growth regulating properties which can result in an increase in the yield of cultivated plants or harvested crops. Further, many compounds of formula I have a growth inhibiting action which is dependent on the concentration. The growth of both monocots and dicots is inhibited. Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Inhibition of the vegetative growth of many cultivated plants permits more plants to be sown in a crop area, so that a higher yield may be obtained per unit of area. A further mechanism of yield increase using growth regulators resides in the fact that nutrients are able to promote flower formation and fruiting to a greater extent, whilst vegetative growth is inhibited.

Inhibition of the vegetative growth of monocot plants, e.g. grasses or also cultivated plants such as cereals, is sometimes desirable and advantageous. Such a growth inhibition is of economic interest, inter alia, in respect of grasses, as the frequency of cutting in flower gardens, parks, sport fields or road shoulders can thereby be reduced. Of importance too is the inhibition of growth of herbaceous and ligneous plants on road shoulders and near transmission lines, or quite generally in areas in which strong growth is undesirable.

The use of growth regulators for inhibiting the growth in height of cereals is also important, as shortening the stalks diminishes or completely eliminates the danger of lodging before harvesting. In addition, growth regulators are able to bring about a strengthening of the stalks in crops of cereals and this too counteracts lodging.

At higher rates of application, all tested plants are so severely damaged in their development that they die.

The invention also relates to herbicidal and plant growth regulating compositions which contain a novel compound of formula I, and also to methods of controlling weeds pre- and postemergence and of inhibiting the growth of monocots and dicots, especially grasses, tropical cover crops and tobacco plant suckers.

The compounds of formula I are used in unmodified form or, preferably, as compositions together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstitued or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethylanolamine salts of dodecylbenzene sulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, N.J., 1981; H. Stache, "Tensid-Taschenbuch" (Handbook of Surfactants), 2nd Edition, C. Hanser Verlag, Munich and Vienna, 1981; M. and J. Ash, "Encyclopedia of Surfactants", Vol. I-III, Chemical Publishing Co., New York, 1980–81.

The compositions usually contain 0.1 to 99%, preferably 0.1 to 80%, of a compound of the formula I, 1 to 99%, of a solid or liquid adjuvant, and 0 to 25%, preferably 0.1 to 25%, of a surfactant.

Preferred formulations are composed in particular of the following constituents (%=percentage by weight):

| Emulsifiable concentrates | |
|---|---|
| active ingredient: | 1 to 50%, preferably 5 to 10% |
| surfactant: | 5 to 30%, preferably 10 to 20% |
| liquid carrier: | 50 to 94%, preferably 70 to 85% |
| Dusts | |
| active ingredient: | 0.1 to 10%, preferably 0.1 to 1% |
| solid carrier: | 99.9 to 90%, preferably 99.9 to 99% |
| Suspension concentrates | |
| active ingredient: | 5 to 75%, preferably 10 to 50% |
| water: | 94 to 25%, preferably 90 to 30% |
| surfactant: | 1 to 40%, preferably 2 to 30% |
| Wettable powders | |
| active ingredient: | 0.5 to 90%, preferably 1 to 80% |
| surfactant: | 0.5 to 20%, preferably 1 to 15% |
| solid carrier: | 5 to 95%, preferably 15 to 90% |
| Granulates | |
| active ingredient: | 0.5 to 30%, preferably 3 to 15% |
| solid carrier: | 99.5 to 70%, preferably 97 to 85%. |

Whereas commercial products will be preferably formulated as concentrates, the end user will normally employ dilute formulations. The formulations can be diluted to a concentration as low as 0.001% of active ingredient. The concentrations are normally from 0.01 to 10 kg a.i./ha, preferably from 0.025 to 5 kg a.i./ha.

The compositions may also contain further auxiliaries such as stabilisers, antifoams, viscosity regulators, binders, tackifiers, as well as fertilisers and other compounds for obtaining special effects.

PREPARATORY EXAMPLE

Example 1

Prepartion of ethyl 4-cyclopropylcarbonyl-3,5-cyclohexanedione-1-carboxylate

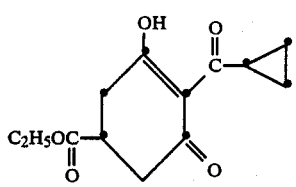

A reaction vessel is charged with 5.4 g of copper cyanide in 40 ml of acetonitrile and then 5.1 ml of cylopropylcarboxylic acid chloride are added dropwise at room temperature, whereupon the reaction temperature rises to 31° C. After everything has been added, the reaction mixture is boiled under reflux for 2½ hours with stirring. The mixture is subsequently cooled to room temperature and 9.2 g of ethyl 3,5-cyclohexanedione-1-carboxylate and 7.1 g of zinc cloride are added. Subsequently at a temperature of 0°–5° C. a solution of 7.4 ml of triethylamine in 10 ml of acetonitrile is added dropwise. The reaction mixture is stirred for about 14 hours (overnight) at room temperature and then 100 ml of cold 4N hydrochloric acid are added. The mixture is then extracted with two 200 ml portions of chloroform, the organic phase is dried over sodium sulfate and concentrated by evaporation and the residue is distilled under high vacuum (bulb tube furnace). A viscous oil distills at 150° C./0.005 mbar and crystallises on standing.

Yield: 7.9 g of crystalline ethyl 4-cyclopropyloxy-3,5-cyclohexanedione-1-carboxylate, m.p. 35.36° C. (Yield=62.7% of theory).

By boiling this ester in 1N sodium hydroxide solution and extracting the cooled solution, 4-cyclopropyloxy-3,5-cyclohexanedione-1-carboxylic acid, which melts at 142°–146° C., is obtained.

In this Example sodium cyanide or potassium cyanide may be used in place of copper cyanide.

The following compounds are obtained in a manner analogous to that of this Example:

TABLE 1

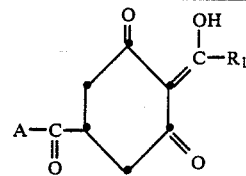

$A = OR_2$

| Comp. | A | $R_1$ | Physical data |
|---|---|---|---|
| 1.01 | $OC_2H$ | $CH_3$ | m.p. 49–51° C. |
| 1.02 | $OC_3H_{7n}$ | $CH_3$ | m.p. 43–44° C. |
| 1.03 | $OCH(CH_3)_2$ | $CH_3$ | m.p. 98–100° C. |
| 1.04 | $OC_4H_{9n}$ | $CH_3$ | $n_D^{20}$ 1.4991 |
| 1.05 | $OCH_2CH(CH_3)_2$ | $CH_3$ | m.p. 39–40° C. |
| 1.06 | $OC(CH_3)_3$ | $CH_3$ | m.p. 76–77° C. |
| 1.07 | $OCH(CH_3)C_2H_5$ | $CH_3$ | m.p. 36–37° C. |
| 1.08 | $OCH_3$ | $C_2H_5$ | m.p. 49–50° C. |
| 1.09 | $OC_2H_5$ | $C_2H_5$ | m.p. 51–52° C. |
| 1.10 | $OC_3H_7$ | $C_2H_5$ | $n_D^{20}$ 1.4960 |
| 1.11 | $OCH(CH_3)_2$ | $C_2H_5$ | m.p. 55–56° C. |
| 1.12 | OH | $C_2H_5$ | m.p. 98–99° C. |
| 1.13 | OH | $C_3H_{7n}$ | m.p. 120–135° C. |
| 1.14 | $OCH_3$ | $C_3H_{7n}$ | $n_D^{20}$ 1.5685 |
| 1.15 | $OC_2H_5$ | $C_3H_{7n}$ | $n_D^{27}$ 1.5060 |
| 1.16 | $OC_3H_{7n}$ | $C_3H_{7n}$ | $n_D^{20}$ 1.5020 |
| 1.17 | $OCH(CH_3)_2$ | $C_3H_{7n}$ | $n_D^{25}$ 1.4998 |
| 1.18 | $OC_4H_{9n}$ | $C_3H_{7n}$ | $n_D^{20}$ 1.4930 |
| 1.19 | $OCH_2CH(CH_3)_2$ | $C_3H_{7n}$ | $n_D^{20}$ 1.4907 |
| 1.20 | $OCH(CH_3)C_2H_5$ | $C_3H_{7n}$ | $n_D^{20}$ 1.4893 |
| 1.21 | $OCH(C_2H_5)_2$ | $C_3H_{7n}$ | $n_D^{20}$ 1.4885 |
| 1.22 | OH | $CH(CH_3)_2$ | m.p. 132° C. |
| 1.23 | $OCH_3$ | $CH(CH_3)_2$ | b.p. 110° C./ 0.01 mbar |
| 1.24 | $OC_2H_5$ | $CH(CH_3)_2$ | $n_D^{20}$ 1.4898 |
| 1.25 | $OC_2H_5$ | $C_4H_{9n}$ | $n_D^{20}$ 1.4943 |
| 1.26 | $OC_2H_5$ | $CH_2CH(CH_3)_2$ | $n_D^{20}$ 1.4948 |
| 1.27 | $OC_2H_5$ | $C_5H_{11n}$ | $n_D^{20}$ 1.4803 |
| 1.28 | $OC_2H_5$ | $C_6H_{13n}$ | $n_D^{20}$ 1.4803 |
| 1.29 | $OC_2H_5$ | $C_7H_{15n}$ | $n_D^{20}$ 1.4773 |
| 1.30 | $OC_2H_5$ | $C_8H_{17n}$ | $n_D^{20}$ 1.4650 |
| 1.31 | $OC_2H_5$ | $C_2H_4Cl$ | |
| 1.32 | $OC_2H_5$ | $C_3H_6Cl$ | |
| 1.33 | $OC_2H_5$ | $C_4H_8Cl$ | |
| 1.34 | $OC_2H_5$ | $CH_2OC_2H_5$ | $n_D^{20}$ 1.5035 |
| 1.35 | $OC_2H_5$ | $CH_2SC_2H_5$ | $n_D^{20}$ 1.5357 |
| 1.36 | OH | $CH_3$ | m.p. 139–141° C. |
| 1.37 | $OCH_3$ | $CH_3$ | m.p. 77–78° C. |
| 1.38 | $OC(CH_3)$ | $C_4H_{9n}$ | m.p. 67–69° C. |
| 1.39 | $OC_2H_4SCH_3$ | $C_3H_{7n}$ | $n_D^{20}$ 1.5170 |
| 1.40 | $OC_2H_5$ | $C_2H_4OCH_3$ | |
| 1.41 | $OC_2H_5$ | $C_2H_4OC_2H_5$ | |
| 1.42 | $OC_2H_5$ | $CH_2OC_3H_{7n}$ | |
| 1.43 | $OC_2H_5$ | $C_2H_4SCH_3$ | |
| 1.44 | $OC_2H_5$ | $CH_2SCH_3$ | |
| 1.45 | OH | $C_2H_4SC_3H_{7n}$ | |
| 1.46 | $OCH_2SCH_3$ | $C_3H_{7n}$ | $n_D^{25}$ 1.5193 |
| 1.47 | $OC_2H_4SCH_3$ | $C_3H_{7n}$ | |
| 1.48 | $OC_2H_4OCH_3$ | $C_3H_{7n}$ | |
| 1.49 | $OC_3H_7i$ | $C_3H_{7n}$ | |
| 1.50 | $OC_3H_6Cl$ | $C_3H_{7n}$ | $n_D^{25}$ 1.4998 |
| 1.51 | benzyloxy | $C_3H_{7n}$ | |
| 1.52 | 3-methoxybenzyloxy | $C_3H_{7n}$ | |
| 1.53 | $OCH_2CH=CH_2$ | $C_3H_{7n}$ | |
| 1.54 | $OCH_2CCl=CH_2$ | $C_3H_{7n}$ | |
| 1.55 | $OCH_2C\equiv CH$ | $C_3H_{7n}$ | |
| 1.56 | $OCH_3$ | $C_6H_{13n}$ | |
| 1.57 | $OC_2H_5$ | cyclopropyl | m.p. 35–56° C. Example 1 |
| 1.58 | $OCH_3$ | cyclohexyl | |
| 1.59 | $OC_6H_{13}$ | $CH_3$ | |
| 1.60 | $OCH_2SCH_3$ | $CH_3$ | |
| 1.61 | $OC_2H_5$ | $CH_2SCH_3$ | |
| 1.62 | $OC_2H_5$ | $C_2H_4OCH_3$ | |
| 1.63 | $OC(CH_3)_3$ | $CHClCH_3$ | |
| 1.64 | $OC_2H_5$ | $CH_2CF_3$ | |
| 1.65 | $OC_2H_5$ | $CH_2CHCl_2$ | |
| 1.66 | $OC_2H_5$ | cyclopentyl | oil |
| 1.67 | $OCH_3$ | cyclobutyl | |
| 1.68 | $OCH_3$ | cyclopentyl | |

TABLE 1-continued

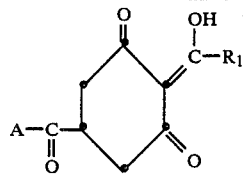

A = OR₂

| Comp. | A | R₁ | Physical data |
|---|---|---|---|
| 1.69 | OC₂H₅ | cyclobutyl | m.p. 60–61° C. |
| 1.70 | OC₂H₅ | cyclopentyl | |
| 1.71 | OCH₃ | cyclohexyl | |
| 1.72 | OC₂H₅ | cyclohexyl | oil |
| 1.73 | OCH₃ | cyclopropyl | m.p. 60–64° C. |
| 1.74 | OC₃H₇n | cyclopropyl | |
| 1.75 | OCH(CH₃)₂ | cyclopropyl | m.p. 70–72° C. |
| 1.76 | OC₄H₉n | cyclopropyl | |
| 1.77 | OCH₂CH(CH₃)₂ | cyclopropyl | |
| 1.78 | OCH(CH₃)C₂H₅ | cyclopropyl | |
| 1.79 | benzyloxy | cyclopropyl | |
| 1.80 | 4-chlorobenzyloxy | cyclopropyl | |
| 1.81 | 2-chlorobenzyloxy | cyclopropyl | |
| 1.82 | cyclohexyloxy | cyclopropyl | |
| 1.83 | OH | cyclopropyl | m.p. 142–146° C. |
| 1.84 | OCH₃ | C(CH₃)₃ | |
| 1.85 | OC₂H₅ | C(CH₃)₃ | m.p. 74–75° C. |
| 1.86 | OH | C(CH₃)₃ | |
| 1.87 | OC₃H₇n | C(CH₃)₃ | |
| 1.88 | OCH(CH₃)₂ | C(CH₃)₃ | |
| 1.89 | OC₂H₅ | C(CH₃)₂CH₂Cl | |
| 1.90 | OCH₃ | C(CH₃)₂CH₂Cl | |
| 1.91 | OCH(CH₃)₂ | C(CH₃)₂CH₂Cl | |
| 1.92 | OC₃H₇n | C(CH₃)₂CH₂Cl | |
| 1.93 | OH | 1-methylcyclopropyl | |
| 1.94 | OCH₃ | 1-methylcyclopropyl | |
| 1.95 | OC₂H₅ | 1-methylcyclopropyl | |
| 1.96 | OCH(CH₃)₂ | 1-methylcyclopropyl | |
| 1.97 | OC₃H₇n | 1-methylcyclopropyl | |
| 1.98 | OC₄H₉n | 1-methylcyclopropyl | |
| 1.99 | OH | cyclopentyl | m.p. 95–103° C. |
| 1.100 | OH | cyclohexyl | m.p. 153–155° C. |
| 1.101 | OH | CH(CH₃)C₂H₅ | m.p. 124–125° C. |
| 1.102 | OH | 1-methylcyclopropyl | m.p. 92–93° C. |
| 1.103 | OC₂H₅ | CH(CH₃)C₂H₅ | oil |

TABLE 2

A = NR₃R₄

| Comp. | A | R₁ | Physical data |
|---|---|---|---|
| 2.01 | NH₂ | C₃H₇n | m.p. 167–169° C. |
| 2.02 | NH₂ | C₂H₅n | |
| 2.03 | N(CH₃)₂ | C₃H₇n | $n_D^{25}$ 1.5290 |
| 2.04 | N(CH₃)₂ | CH(CH₃)₂ | m.p. 60–62° C. |
| 2.05 | NHC₄H₉ iso | CH(CH₃)₂ | m.p. 126–128° C. |
| 2.06 | NHC₄H₉ iso | CH₃ | |
| 2.07 | N(CH₂—CH=CH₂)₂ | cyclopropyl | |
| 2.08 | NHCH₂—C≡CH | CH₂OCH₃ | |
| 2.09 | benzylamino | C₃H₇n | wax |
| 2.10 | 3-nitrobenzylamino | C₂H₄Cl | |
| 2.11 | 1-methylphenylethylamino | C₂H₄OC₂H₅ | |
| 2.12 | NHC₂H₄SC₂H₅ | CH₂CH(CH₃)₂ | |
| 2.13 | piperidino | CH(CH₃)₂ | |
| 2.14 | morpholino | C₆H₁₃n | |
| 2.15 | N(CH₃)₂ | cyclopropyl | m.p. 109–112° C. |
| 2.16 | benzylamino | cyclopropyl | m.p. 130–144° C. |

TABLE 2-continued

A = NR₃R₄

| Comp. | A | R₁ | Physical data |
|---|---|---|---|
| 2.17 | anilino | cyclopropyl | |
| 2.18 | 3-trifluoromethylanilino | cyclopropyl | |
| 2.19 | N(CH₃)OCH₃ | C₃H₇n | oil |
| 2.20 | N(CH₃)OCH₃ | C₂H₅ | |
| 2.21 | anilino | C₃H₇n | m.p. 123–127° C. |
| 2.22 | anilino | CH₃ | |
| 2.23 | anilino | C₆H₁₃n | |
| 2.24 | anilino | C₂H₄CH(CH₃)₂ | |
| 2.25 | 3-trifluoromethylanilino | C₃H₇n | |
| 2.26 | 4-methoxyanilino | C₃H₇n | |
| 2.27 | 4-chloroanilino | CH₃ | |
| 2.28 | N(C₂H₅)₂ | C₃H₇n | oil |
| 2.29 | NHCH₃ | C₃H₇n | m.p. 157–159° C. |
| 2.30 | N—methylanilino | C₃H₇n | oil |
| 2.31 | cyclopropylamino | C₃H₇n | |
| 2.32 | NHC₆H₁₃n | C₃H₇n | |
| 2.33 | NHC₂H₄SCH₃ | C₃H₇n | wax |
| 2.34 | NHC₂H₄SCH₃ | C₂H₅ | |
| 2.35 | NHC₂H₄SC₃H₇i | C₃H₇n | |
| 2.36 | pyrrolidino | C₃H₇n | wax |
| 2.37 | N(CH₂CH=CH₂)₂ | C₃H₇n | m.p. 61–67° C. |
| 2.38 | N(CH₃)₂ | cyclobutyl | m.p. 76–78° C. |
| 2.39 | N(CH₃)₂ | C₆H₁₃n | |
| 2.40 | N(CH₃)₂ | cyclobutyl | m.p. 76–78° C. |
| 2.41 | NHC₃H₆SCH₃ | C₃H₇n | wax |
| 2.42 | N(CH₃)₂ | C₂H₅ | m.p. 89–91° C. |
| 2.43 | N(CH₃)₂ | C(CH₃)₃ | |
| 2.44 | benzylamino | C(CH₃)₃ | |
| 2.45 | N(CH₃)₂ | C₅H₁₁n | m.p. 70–72° C. |
| 2.46 | N(CH₃)₂ | 1-methylcyclopropyl | m.p. 70–71° C. |
| 2.47 | anilino | 1-methylcyclopropyl | |
| 2.48 | 1-methylanilino | 1-methylcyclopropyl | |
| 2.49 | NHC(CH₃)₃ | 1-methylanilino | |
| 2.50 | N(CH₃)₂ | CH₃ | m.p. 118–120° C. |

FORMULATION EXAMPLES

Example 2

Formulation Examples for liquid active ingredients of formula I (throughout, percentages are by weight)

| (a) Emulsifiable concentrates | (a) | (b) | (c) |
|---|---|---|---|
| active ingredient | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| xylene mixture | 70% | 25% | 20% |

Emulsions of any required concentration can be produced from such concentrates by dilution with water.

| (b) Solutions | (a) | (b) | (c) | (d) |
|---|---|---|---|---|
| active ingredient | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum distillate (boiling range 160–190°) | — | — | 94% | — |

These solutions are suitable for application in the form of micro-drops.

| (c) Granulates | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| (d) Dusts | (a) | (b) |
|---|---|---|
| active ingredient | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Example 3

Formulation examples for solid active ingredients of formula I (throughout, percentages are by weight)

| (a) Wettable powders | (a) | (b) |
|---|---|---|
| active ingredient | 20% | 60% |
| sodium lignosulfonate | 5% | 5% |
| sodium lauryl sulfate | 3% | — |
| sodium diisobutylnaphthalenesulfonate | — | 6% |
| octylphenol polyethylene glycol ether (7–8 moles of ethylene oxide) | — | 2% |
| highly dispersed silicic acid | 5% | 27% |
| kaolin | 67% | — |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | |
|---|---|
| active ingredient | 10% |
| octylphenol polyethlene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| (c) Dusts | (a) | (b) |
|---|---|---|
| active ingredient | 5% | 8% |
| talcum | 95% | — |
| kaolin | — | 92% |

Ready-for-use dusts are obtained by mixing the active ingredient with the carrier, and grinding the mixture in a suitable mill.

| (d) Extruder granulate | |
|---|---|
| active ingredient | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| (e) Coated granulate | |
|---|---|
| active ingredient | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | |
|---|---|
| active ingredient | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

BIOLOGICAL EXAMPLES

Example 4

Growth inhibition of cereals

Summer barley (*Hordeum vulgare*) and summer rye (*Secale*) are sown in sterilised soil in plastic pots in a greenhouse and watered as required. The cereal shoots are treated about 21 days after sowing with an aqueous spray mixture of a compound of formula I. The concentration of test compound corresponds to 0.1 to 2.5 kg of active ingredient per hectare. Evaluation of the growth of the cereals is made 10 and 21 days after application. A comparison with untreated controls shows that the growth of cereal plants treated with compounds of formula I is significantly reduced. The compounds of Tables 1 and 2 prove particularly effective.

Example 5

Growth inhibition of grasses

Seeds of the grasses *Lolium perenne, Poa pratensis, Festuca ovina* and *Cynodon dactylon* are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture of a compound of formula I. The concentration of test compound corresponds to 0.1 to 2.5 kg a.i. per hectare. The growth of the grasses is evaluated 10 and 21 days after application. The compounds of Table 1 effect a marked reduction in growth. Compound 1.1 effects a particularly marked growth inhibition and reduces new growth almost completely (growth rate 0 to 10%).

Example 6

Increase in yield of soybeans

Soybeans of the "Hark" variety are sown in plastic containers in an earth/peat/sand mixture (6:3:1). The containers are put into a climatic chamber and the plants develop to the 5-6 trefoil leaf stage after about 5 weeks by optimum control of temperature, light, fertiliser addition, and watering. The plants are then sprayed with an aqueous mixture of a compound of formula I until thoroughly wetted. The concentration of test compound corresponds to up to 500 ppm of active ingredient. Evaluation is made about 5 weeks after application. Compared with untreated controls, the compounds of formula I markedly increase the number and weight of the harvested siliquae. The compounds of Tables 1 and 2 prove particularly effective.

Example 7

Growth inhibition of cover crops

Test plants of the varieties *Centrosema plumieri* and *Centrosema pubescens* are reared from cuttings in plastic pots filled with an earth/turf/sand mixture (1:1:1). After they have grown roots, the plants are transplanted into 9 cm pots and watered as required. For further growth the plants are then kept in a greenhouse at a day temperature of 27° C. and a night temperature of 21° C. The average light exposure is 14 hours (6000 lux) and the humidity is 70%. The plants are cut back to a height of about 15 cm and sprayed 7 days later with a spray mixture of the test compound (corresponding to a concentration of 0.3 and 3 kg a.i./ha respectively). Four weeks after application the growth of the plants is compared with that of untreated control plants which have been cut back. The test shows that the compounds of Table 1 effect a marked growth inhibition of the cover plants.

Example 8

Inhibition of senescence in cereal plants

Summer wheat of the "Svenno" variety is sown in pots with compost soil and reared without special climatic conditions. About 10 days after emergence, 10 to 12 cm primary leaves are cut off and put individually into the test tubes containing 10 ml of suspension of test compound (1.25 to 10 ppm of active ingredient). The test tubes are kept in a climatic room at 23° C. and 70% relative humidity and irradiated daily for an average of 14 hours (10,000 lux). Evaluation of the inhibition of senescence is made 7 days later by comparing the degree of yellowing with still fresh, green leaves. This test shows that these compounds markedly inhibit the senescence of the test plants. In particular the compounds of Tables 1 and 2 inhibit yellowing of the leaves during the test period.

What is claimed is:

1. A process for the preparation of a 4-acyl-3,5-cyclohexanedione-1-carboxylic acid derivative of formula I

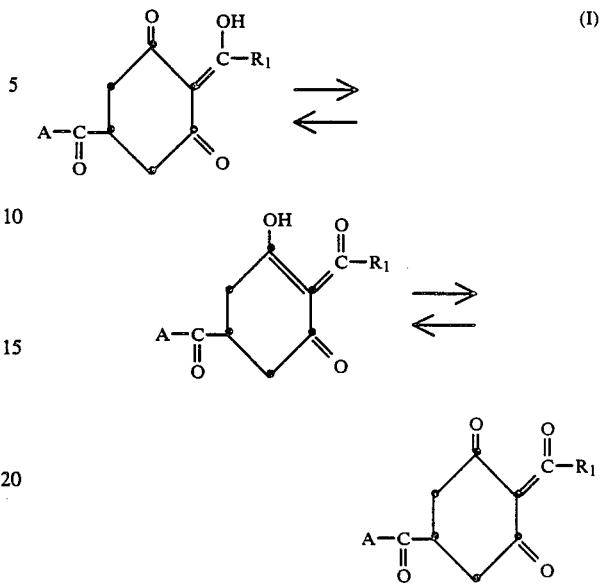

wherein

A is an $OR_2$ or $-NR_3R_4$ radical or a metal or ammonium salt thereof, $R_1$ is $C_1-C_6$alkyl or $C_3-C_6$cycloalkyl, each unsubstituted or substituted by halogen, $C_1-C_4$alkoxy or $C_1-C_4$alkylthio, $R_2$, $R_3$ and $R_4$ are each independently hydrogen, $C_1-C_6$alkyl, $C_1-C_4$haloalkyl, $C_2-C_{10}$alkoxyalkyl, $C_2-C_{10}$alkylthioalkyl; $C_3-C_6$alkenyl which is unsubstituted or substituted by halogen, $C_1-C_4$alkoxy or $C_1-C_4$alkylthio; $C_3-C_6$alkynyl; or phenyl wherein the phenyl nucleus is unsubstituted or substituted by halogen, $C_1-C_4$alkyl, $C_1-C_4$alkoxy, $C_1-C_4$haloalkyl, nitro or cyano, and $R_3$ and $R_4$, together with the nitrogen atom to which they are attached, also form a 5- or 6-membered heterocyclic ring system which may contain an additional oxygen or sulfur atom in the ring, which process comprises combining, in an inert solvent, a reactive carboxylic acid derivative of formula III

wherein X is a halogen atom, an alkylsulfonic or arylsulfonic acid radical or the molecular radical

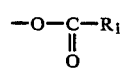

which is necessary to form an anhydride and $R_1$ is as defined for formula I, and a metal cyanide, heating the reaction mixture to boiling point and, after cooling to a temperature in the range from 0° C. to room temperature, adding in succession to said mixture a Lewis acid, an equimolar amount, with respect to the carboxylic acid derivative of formula III, of a 3,5-cyclohexanedione-1-carboxylic acid derivative of formula II

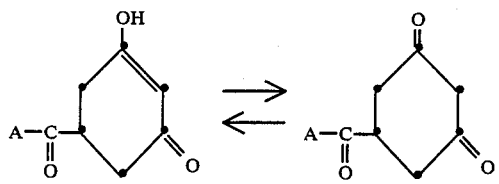

wherein A is as defined for formula I, and, gradually, an organic base and, after acidifying the reaction mixture with an aqueous acid, isolating therefrom by extraction the 4-acyl-3,5-cyclohexanedione-1-carboxylic acid derivative of formula I.

2. A process according to claim 1, wherein the inert organic solvent is acetonitrile or a halogenated hydrocarbon.

3. A process according to claim 1, wherein the reactive carboxylic acid derivative of formula III is a halide.

4. A process according to claim 1, wherein the metal cyanide is an alkali metal cyanide or copper cyanide.

5. A process according to claim 1, which comprises heating the mixture of organic solvent, carboxylic acid derivative of formula II and metal cyanide for 1 to 25 hours under reflux before cooling to a temperature in the range from 0° C. to room temperature and continuing the reaction sequence.

6. A process according to claim 1, wherein the Lewis acid is zinc chloride or aluminium chloride.

7. A process according to claim 1, wherein diethylamine, trimethylamine, triethylamine, γ-picoline, 4-N,N-dimethylpyridine, 4-N,N-diethylpyridine, 4-pyrrolidinopyridine, N-methylimidazole or 4-ethylimidazole is added gradually as organic base to the reaction mixture.

8. A process according to claim 1, which comprises acidifying the reaction mixture with a mixture of hydrochloric acid and ice.

9. A process according to claim 1, wherein the reactive carboxylic acid derivative of formula III is the chloride.

* * * * *